United States Patent [19]

Turtschan

[11] Patent Number: 4,622,800
[45] Date of Patent: Nov. 18, 1986

[54] STERILIZING METHOD AND APPARATUS

[75] Inventor: Alfons Turtschan, Schwäbisch Hall, Fed. Rep. of Germany

[73] Assignee: Gasti-Verpackungsmaschinen GmbH, Fed. Rep. of Germany

[21] Appl. No.: 749,009

[22] Filed: Jun. 26, 1985

Related U.S. Application Data

[63] Continuation of Ser. No. 377,636, May 12, 1982, abandoned.

[30] Foreign Application Priority Data

May 13, 1981 [DE] Fed. Rep. of Germany ........ 3119037

[51] Int. Cl.[4] ............................................. B65B 55/02
[52] U.S. Cl. ....................................... 53/425; 53/167; 422/303
[58] Field of Search .................. 53/90, 167, 274, 425, 53/426, 432, 510; 422/300, 302, 303, 310

[56] References Cited

U.S. PATENT DOCUMENTS

| 1,083,465 | 1/1914 | Sawyer | 422/303 |
|---|---|---|---|
| 2,491,015 | 12/1949 | Poole | 422/303 X |
| 3,606,995 | 9/1971 | Hemel | 53/425 X |
| 3,783,581 | 1/1974 | Pierce | 53/426 |
| 3,859,774 | 1/1975 | Bausch | 53/167 |
| 3,996,725 | 12/1976 | Walles | 53/510 X |
| 4,032,297 | 6/1977 | Lyshkow | 422/91 |
| 4,035,981 | 7/1977 | Braun et al. | 53/167 X |
| 4,056,921 | 11/1977 | Gilliand et al. | 53/167 |
| 4,152,464 | 5/1979 | Brody et al. | 53/167 X |
| 4,166,563 | 9/1979 | Peyraud et al. | 198/619 |
| 4,442,611 | 4/1984 | Gunther et al. | 34/156 X |

FOREIGN PATENT DOCUMENTS

| 0753069 | 1/1971 | Belgium | 422/302 |
|---|---|---|---|
| 0045389 | 2/1982 | European Pat. Off. . | |
| 1492421 | 1/1970 | Fed. Rep. of Germany . | |
| 1934363 | 1/1971 | Fed. Rep. of Germany . | |
| 1642069 | 6/1971 | Fed. Rep. of Germany . | |
| 1617967 | 4/1972 | Fed. Rep. of Germany . | |
| 2164500 | 6/1973 | Fed. Rep. of Germany . | |
| 2724721 | 12/1977 | Fed. Rep. of Germany . | |
| 2841002 | 3/1979 | Fed. Rep. of Germany . | |
| 2835243 | 2/1980 | Fed. Rep. of Germany . | |
| 2919015 | 11/1980 | Fed. Rep. of Germany . | |
| 3016266 | 10/1981 | Fed. Rep. of Germany . | |
| 3031084 | 3/1982 | Fed. Rep. of Germany . | |
| 3029685 | 3/1982 | Fed. Rep. of Germany . | |

Primary Examiner—John Sipos
Assistant Examiner—Steven P. Weihrouch
Attorney, Agent, or Firm—Steele, Gould & Fried

[57] ABSTRACT

According to the method of the invention the packing means, for example yoghurt containers, are introduced into a sterilizing chamber, which is sealed. The interior of the chamber is then evacuated and then pressurized steam is intoduced into it. This leads to a temperature rise and consequently to a sterilization of the packing means. The steam is only introduced for a brief period, e.g. for 5 seconds. The sterilizing chamber is then evacuated again and steam and condensate are removed. Cold sterile air is then blown into the chamber, which leads to a fast cooling of the packing means.

14 Claims, 8 Drawing Figures

STERILIZING METHOD AND APPARATUS

This is a continuation of application Ser. No. 377,636 filed May 12, 1982, now abandoned.

The invention relates to a method for sterilizing packing means, particularly plastic cups and covering foil for cups prior to the filling and sealing in a sterile filling and sealing machine, wherein the packing means are introduced into a sealable sterilizing chamber which, before and/or after the actual sterilization, is optionally evacuated by means of saturated steam or some other gaseous or vapourous sterilizing medium. The invention also relates to an apparatus for performing the method.

DAS No. 19 34 363 discloses a method wherein containers to be sterilized are introduced into a sterilizing chamber, which is sealed and evacuated. A sterilizing gas is then introduced into the sterilizing chamber and it is then exposed to several successive powerful pressure fluctuations. Subsequently a second evacuation removes the sterilizing gas again before filling the sterilizing chamber with the sterile atmosphere of the packaging machine. The treatment period lasts about 15 minutes.

It is known from DOS No. 29 19 015 in the case of a continuously operating filling machine to move the cups through a sterilizing station, in which they are treated with a sterile steam-air mixture and then with sterile hot air. The cups are only treated from the inside, so that the mixture must be heated to about 275° C. and is used twice. The hot air, which also has to be blown twice into the containers, must be heated to approximately 250° C. The disadvantage of this apparatus is that initially the unsterile containers are introduced into the sterile chamber, where they are sterilized from above. However, this means that there is always a risk of the actual filling chamber becoming non-sterile. In addition, high energy levels are required to obtain the requisite high temperatures.

It is also known (DOS No. 28 35 243) to sterilize web-like, flexible packing materials with set steam under pressure at a temperature of approximately 125° C. to approximately 150° C. However, the plastic material is not deformable. Therefore deformation cannot occur as a result of heat action.

The object of the invention is to provide a method of the aforementioned type permitting a sterilization which is satisfactory in all respects with minimum energy and time expenditure and without special demands having to be made on the packaging materials with respect to the thermal stability.

It is also a object of the invention to provide an apparatus for performing this method. According to the invention this object is achieved in that the packing means are introduced into the sterilizing chamber which is sealed from the sterile area of the filling and sealing machine, the inlet side of the sterilizing chamber is then sealed and, following their sterilization, the sterilized packing means are directly introduced into the filling and sealing machine by opening the outlet side with the inlet side closed.

The packing means pass through a sluice into the sterilizing chamber, where they are sterilized and then pass through a further sealable opening into the filling and sealing machine. In particular saturated stem can be used for sterilization purposes and in certain cases need only act for a very short time, because it suffices if the temperature necessary for sterilization only occurs on the surface of the packing means. The brief heating period means a considerable energy saving and much faster working. In timed manner the sterilizing chamber is converted from a non-sterile chamber by sterilization into a sterile chamber. It is possible that following evacuation after steam introduction, sterile air can be blown in under a slight overpressure. This blowing-in action ensures that no germs can penetrate from the atmosphere. It is particularly advantageous if, after introducing the steam, the latter is blown out with the aid of sterile air. This obviates the second evacuation and leads to a faster cooling of the chamber and its content.

The temperatures to be applied and the duration of steam sterilization are dependent on the articles to be packed with the packing means. It is also possible to introduce the steam under pressure.

According to the invention, when sterilizing containers, they are sterilized with the opening downwards and are then turned over again for filling purposes. This ensures that no condensate can be left behind in the containers.

The invention also proposes an apparatus for sterilizing packing means prior to their filling and sealing, particularly for performing the method according to the invention having a sterilizing chamber with in each case one tightly sealable inlet and outlet port, as well as with connections for vacuum, sterilising agent and inert gas, whilst according to the invention the outlet port of the sterilizing chamber is directly connected to the filling machine inlet. Thus, the sterilizing chamber forms a type of sluice, which ensures that in all circumstances only sterile objects can enter the filling and sealing machine. The inlet and outlet port can be sealable by slides contactable under the action of an eccentric and/or contact rollers. The contacting of the slides leads to improved sealing and simultaneously this permits the easier moving of the slides in the uncontacted state.

According to another feature of the invention the inert gas and sterilizing agent connection leads into a distributing chamber surrounding the sterilizing chamber in an annular manner and from where the gas and sterilizing agent passes in uniformly distributed manner into the sterilizing chamber through a plurality of openings.

According to the invention the vacuum connection is located in the vicinity of the lowest point of a trough, which has the advantage that condensate, which is preferably separated towards the bottom, is also removed.

To permit satisfactory working even in the case of stacked cups, according to another feature of the invention the latter have stacking recesses, notches, etc., so that they do not stick to one another.

Further features, details and advantages of the invention can be gathered from the claims, the following description of preferred embodiments and the attached drawings, wherein:

FIG. 6 is a graph of the course of the method according to the invention.

FIG. 7 is a graph corresponding to FIG. 6 of another embodiment.

Figure 1:
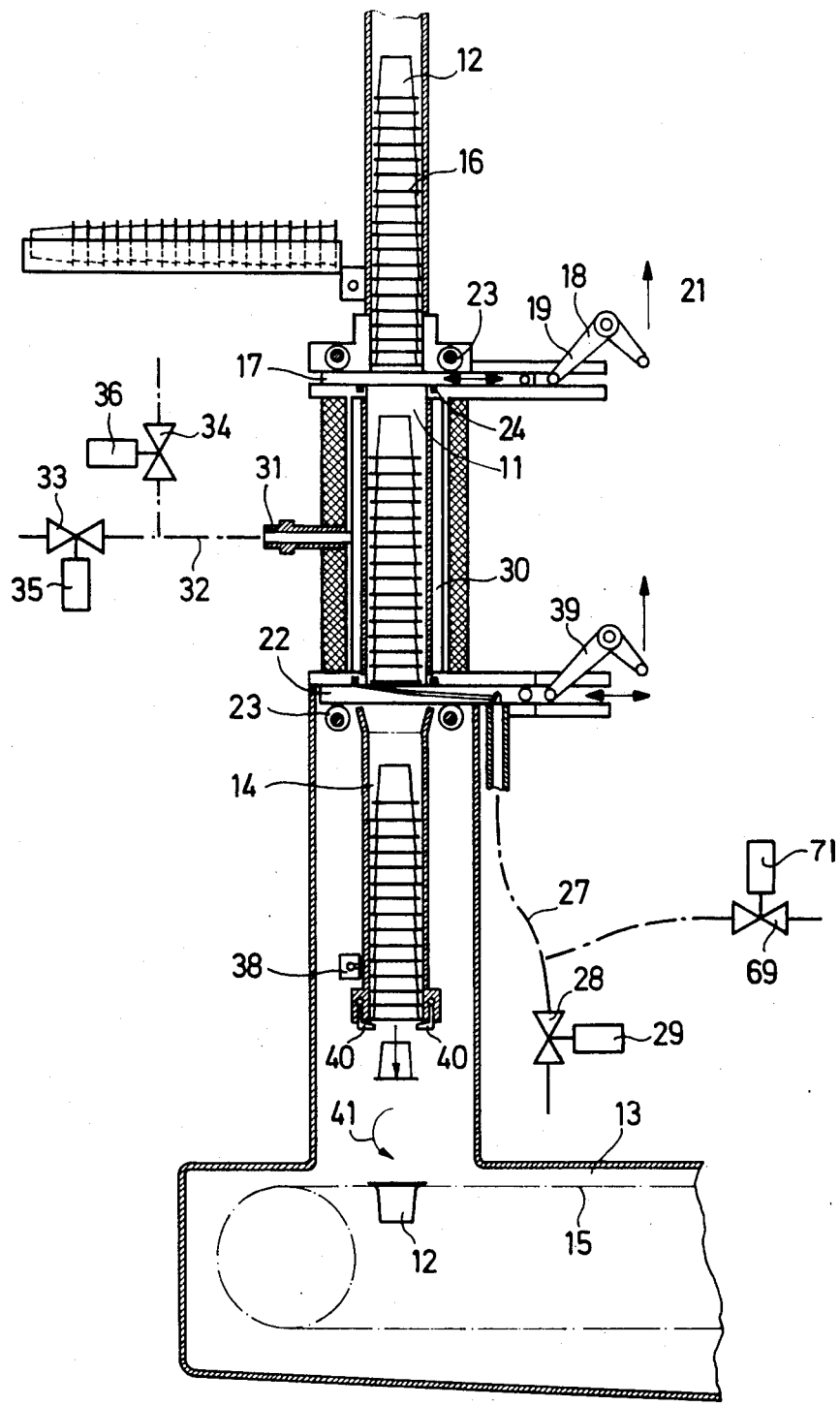
FIG. 1 is a section through a diagrammatic view of an apparatus for performing the method according to the invention.

The apparatus for performing the method according to the invention shown in FIG. 1 comprises a sterilizing chamber 11 into which cups 12 which are to be sterilized therein are introduced from above. The sterilizing chamber is positioned above a filling machine 13 in which the sterilized cups are held ready in an unstacking magazine 14. From unstacking magazine 14 the cups are individually removed, turned over by 180° and introduced into a diagrammatically shown conveyor belt 15. Cups 12 are positioned above sterilizing chamber 11 in a stacking magazine 16. The lowermost cup 12 is positioned on a slide 17, which seals the inlet to the sterilizing chamber 11 and which can be moved to the right with the aid of a toggle lever 18, so that it frees the inlet to chamber 11. Toggle lever 18 is pivotably connected to slide 17 by one end of its left-hand arm 19, whilst the end of the right-hand arm of toggle lever 18 is movable in the direction of arrow 21 with the aid of a not shown means, e.g. a motor.

On freeing the upper opening of sterilizing chamber 11 by slide 17, the cups fall into the chamber 11, after which the latter is closed again. Closure is brought about in that slide 17 and a corresponding slide 22 provide on the bottom of sterilizing chamber 11 are brought into the position shown in FIG. 1, after which the eccentrics 23 are brought by an also not shown device into the position shown in FIG. 1. In this position the eccentrics 23 push the particular slide against a seal 24 in the top or bottom of sterilizing chamber 11.

Figure 2:
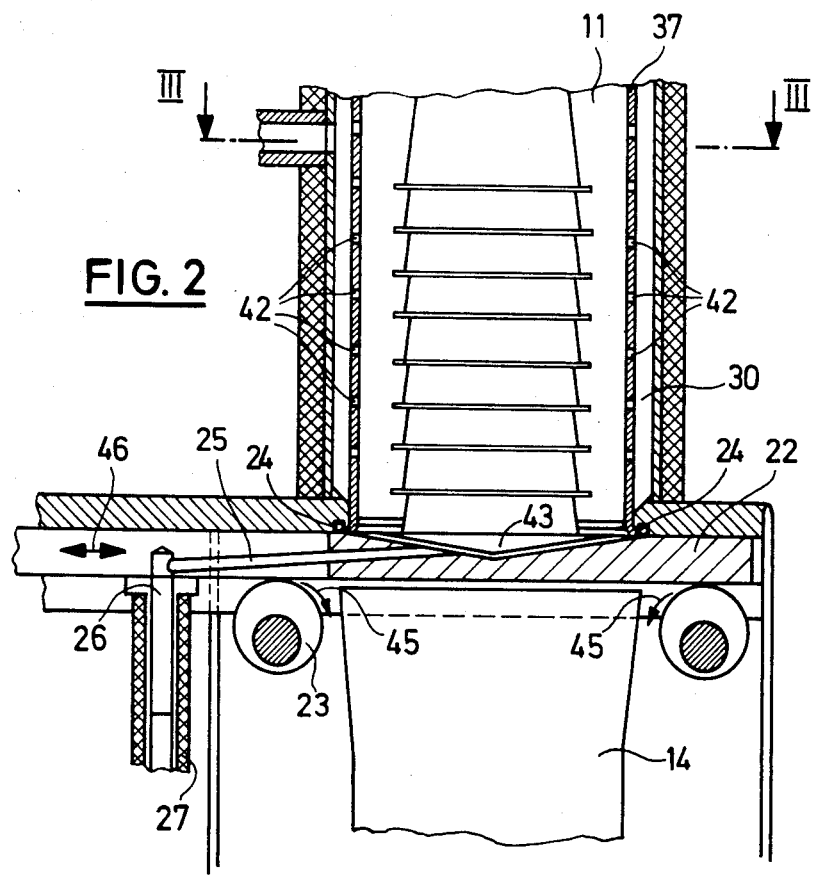
FIG. 2 is a sectional view of a detail of the apparatus of FIG. 1.

Slide 22 has a sloping bore 25, which passes into a connection 26 for a hose or the like, cf. in detail FIG. 2. Line 27 connected to connection 26 contains two valves 28, 69, which are opened and closed by two control devices 29, 71, which are not shown in detail. Valve 28 leads to a vacuum pump, while valve 69 leads into the atmosphere.

Sterilizing chamber 11 is surrounded by an annular distributing chamber, into which issues a connection 31, to which is connected a diagrammatically indicated line 32, which branches towards two valves 33, 34. A control device 35 or 36 is associated with each of the valves and serves to open and close the latter. Valve 34 is used for introducing sterile air and a valve 33 for introducing steam.

The partition 37 between distributing chamber 30 and sterilizing chamber 11 contains individual openings distributed over the periphery and/or length of chamber 11, which permit a distributed introduction of steam of sterile air from distributing chamber 30 into sterilizing chamber 11.

The apparatus according to the invention is operated in the following way. Firstly slide 17 is moved to the right, so that the upper opening of the sterilizing chamber 11 is freed. The cups 12 arranged in the stacking magazine 16 then slide into the interior of sterilizing chamber 11, which consequently becomes non-sterile. The upper slide 17 is then moved by toggle lever 18 back into the position shown in FIG. 1, after which the eccentric 23 for slide 17 presses the latter against seal 24. The lower slide 22 is already in the contacted position, so that now sterilizing chamber 11 is sealed. Control device 29 now opens valve 28, so that sterilizing chamber 11 is evacuated by means of line 27. With the aid of a not shown control device valve 33 is opened by means of control device 35, so that hot air can now penetrate the interior of sterilizing chamber 11 and at this time valve 28 is still open. Shortly afterwards valve 28 is closed, so that pressure can now build up in sterilizing chamber 11, which leads to a rise of the steam temperature. As soon as the desired temperature has been reached in sterilizing chamber 11, which can be established by a thermometer probe or on a time-dependent basis, valve 33 closes again. Simultaneously valve 28 is opened again with the aid of the associated control device 29, so that now steam and possibly formed condensate are sucked out of the sterilizing chamber 11. After a short time valve 34 is opened with the aid of the associated control device 36 and now cold sterile air flows through sterilizing chamber 11 into line 27 to valve 28, so that the cups 12 are cooled again. This ensures that the temperature on the surface of the cups is not dissipated into the interior of the cup walls. This rapid cooling by the sterile air has the advantage that there can be no deformation of the cups and that the method can be performed as rapidly as possible. Valve 28 is then closed, whilst valve 34 remains open.

There is now a certain overpressure in sterilizing chamber 11, which is maintained by the sterile air. As soon as a contact 38 at the end of unstacking magazine 14 establishes that there are only a few further cups in the magazine, the eccentric 23 for the lower slide 22 is released, the slide is moved to the right with the aid of the associated toggle lever 39, so that the cups 12 can drop out of the sterilizing chamber into the unstacking magazine 14. At this time the entire interior of the sterilizing chamber 11 is sterile, so that no germs can penetrate the filling machine 13. This is also aided by maintaining the slight overpressure with sterile air prior to opening the lower slide 22.

At the bottom of the unstacking magazine the cups are individually removed with the aid of claws 40, are gripped by a not shown holder and turned over, as is indicated by arrow 41. The opening of the containers is now at the top, so that they can be inserted into conveyor belt 14, from where they can be conveyed to the filling stations.

FIG. 2 more precisely shows the lower part of sterilizing chamber 11. It can be seen that sterilizing chamber 11 is surrounded by distributing chamber 30, the partition 37 having individual holes, 42.

Figure 3:
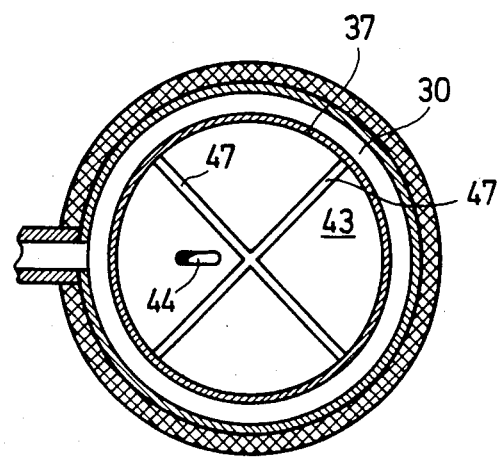
FIG. 3 is a section approximately along line III—III of FIG. 2.

On its top, lower slide 22 has a trough 43 arranged concentrically to the circular cylindrical sterilizing chamber 11, cf. also FIG. 3. Bore 25 issues into trough 43 and opening 44 is arranged approximately in the centre of said trough 43. Therefore condensate, which has collected in trough 43, can be removed by line 27.

FIG. 2 also clearly shows that the two eccentrics, which can be turned in the direction of arrows 45, can press the slide 22 against a seal 24. When eccentrics 23 are turned, slide 22 can move in the direction of the double arrow 46.

FIG. 3 shows that trough 43 contains ribs 47 which are at right angles to one another and serve to provide a punctiform support for the in each case lower cup 12. It would naturally also be possible to provide a linear support, if the line was not closed. This ensures that line 27 only evacuates the interior of the lowermost cup.

Figure 4:
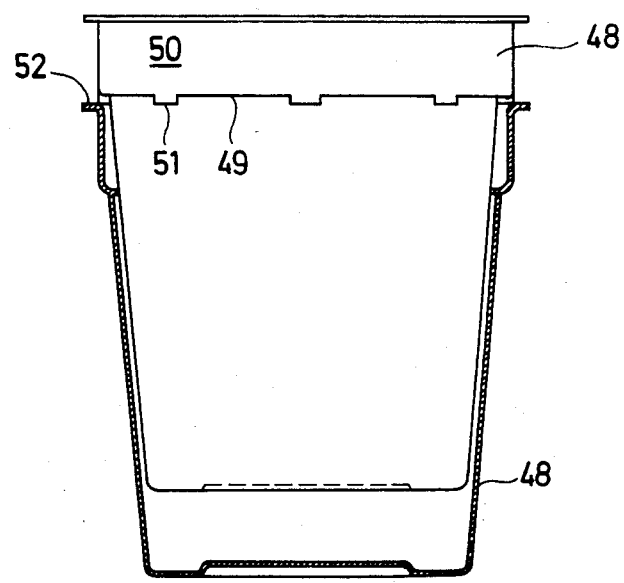
FIG. 4 is a part sectional side view of two cups.

FIG. 4 shows two cups 48 stacked inside one another, the upper cup 48 being shown in side view and the lower cup in section. It can be seen that the sides of the cups 48 have a certain distance from one another, so that this does not impede the introduction of the steam into the cups. On the underside 49 of its upper cylindrical portion 50, cups 48 have individual stacking recesses 51, which engage on the upper rim 52 of the in each case lower cup 48. Thus, steam can enter the lower cup 48 between the individual stacking recesses 51.

Figure 5:
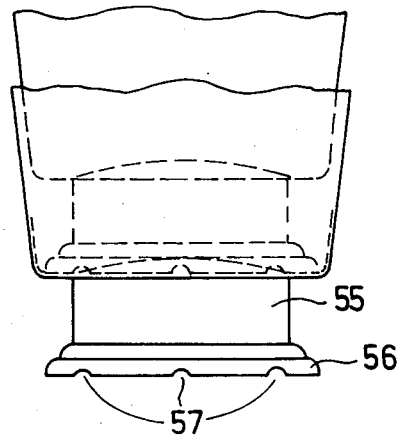
FIG. 5 is a partial view of two other cups.

FIG. 5 diagrammatically shows two further cups 54 having a hollow base 55. In this case the lower edge of base 55 is provided with individual notches 57, which also serve to provide access to the interior of the hollow base 55 in the stacked state. This not only facilitates the penetration of steam, but also prevents sticking together of the cups under the action of pressure. Thus, here again a puntiform support or engagement is ensured.

Figures 6, 7:
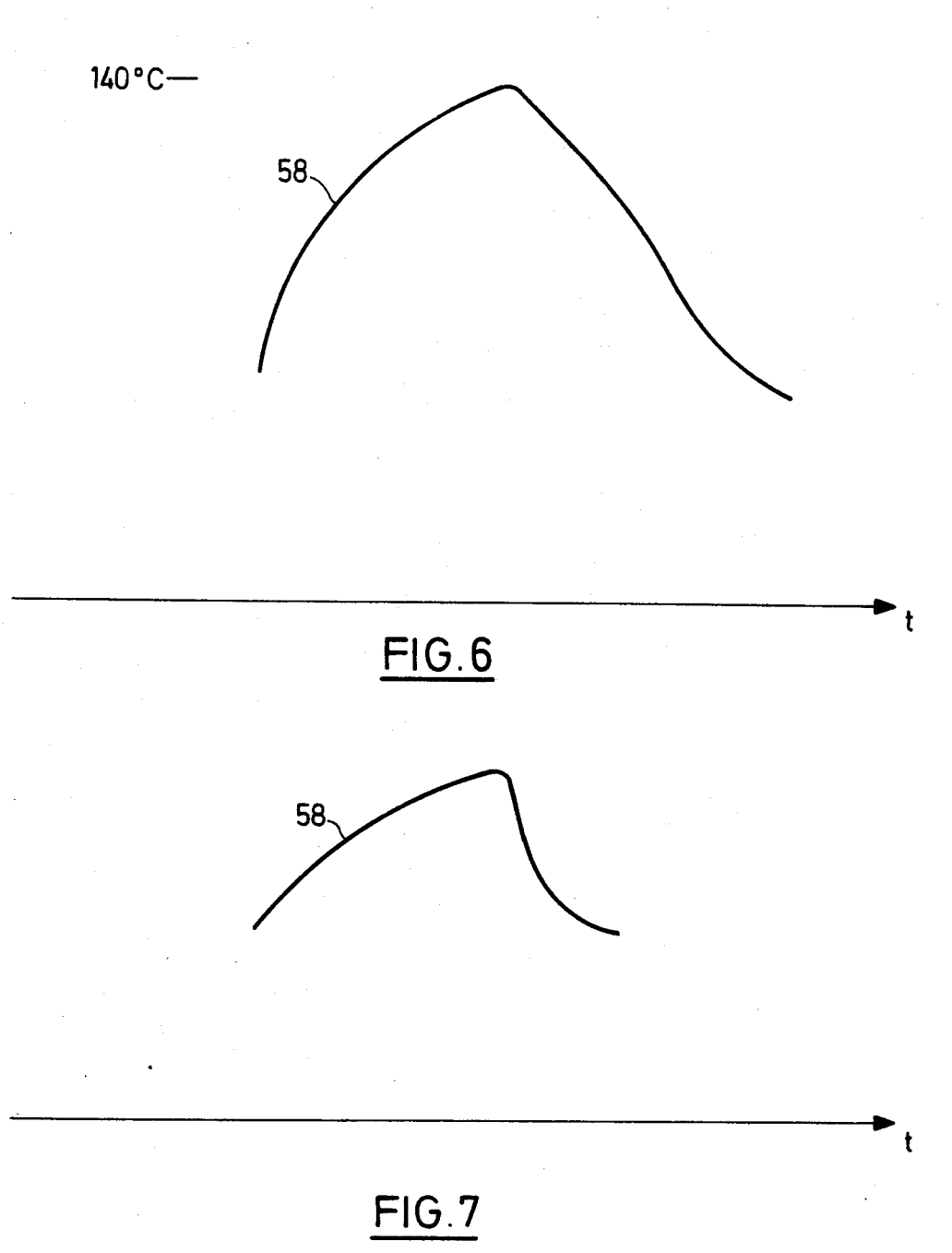

FIG. 6 shows in graph form the performance of the method, the bar chart of the lower part of FIG. 6 showing the time sequence of the individual stages of the method. The length of the bars corresponds to the length of the individual stages. The upper part of FIG. 6 shows with the aid of curve 58 the temperature gradient in the sterilizing chamber 11. It can be seen that after introducing the steam, there is a temperature rise to about 140° C. after which, starting with the opening of valve 28, there is again a pressure drop to the starting temperature.

In the case of the method shown in FIG. 7, following the introduction of steam, sterile air is immediately blow in. By opening valve 69, cf. FIG. 1, the steam is immediately blown out into the atmosphere. This realization of the method according to the invention has the advantage that the interior of sterilizing chamber 11 and its content are more rapidly cooled, which is made apparent by the steeper slope of the curve in the upper part of FIG. 7. Instead of removing the steam and sterile air into the atmosphere, it would also be possible to return the same into the sterile air supply.

Figure 8:
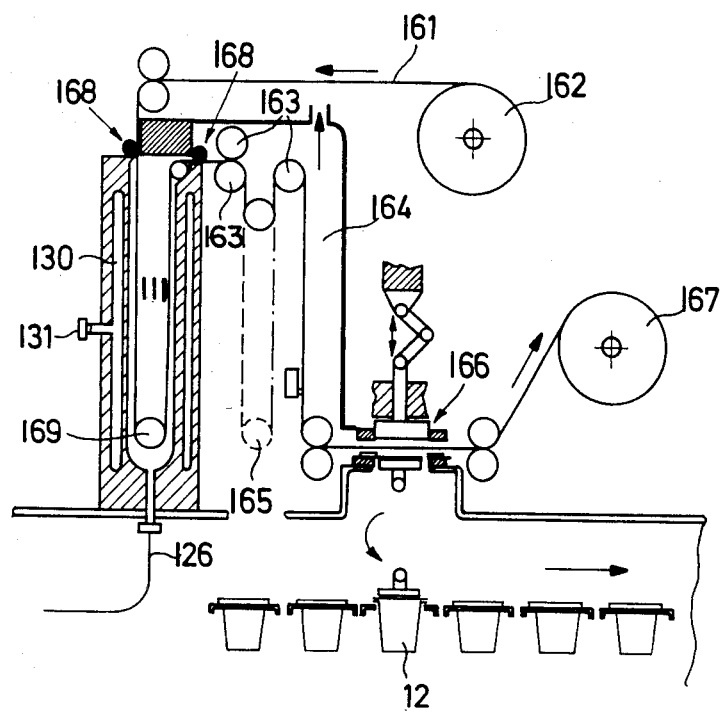
FIG. 8 is a diagrammatic view of an apparatus according to the invention for treating strip material.

In the case of the apparatus for sterilizing packing means according to FIG. 8, it is of the type which can process strip-like plastic foil. Plastic foil 161 is pased from a delivery reel 162 through sterilizing chamber 111, after which the foil 161 reaches an area 164, which is permanently sterile. Area 164 contains a plurality of guide rollers 163 and a compensating roller 165. From area 164 foil 161 passes to a punching device 166, which punches covers from foil 161 with the aid of two punches and the remainder of the foil 161 is then wound up on to a second reel 167.

The foil enters and leaves sterilizing chamber 111 with the aid of slots, which can be sealed by rubber rollers 168. The continuous foil still remains in the slots in the sealed state. The foil is led into sterilizing chamber 111 by means of a guide roller 169, foil 161 being conveyed intermittently through chamber 111. Thus, one portion of the foil is always secured and is processed in sterilizing chamber 111, as has already been described with reference to FIG. 1. When it is in sterilizing chamber 111, the foil is intermittently moved past the punching device 166 in short time cycles and the covers are punched out of the foil. During this timed advance of the foil, the compensating roller 165 is raised in area 164 until the sterilizing process is ended. Then, with the aid of the guide roller, foil 61 is advanced by the sterilized amount and then by means of compensating roller 164 a supply is again formed in sterile area 164.

The container covers punched from the foil are placed and fixed to the filled containers 12 in the processing machine.

Sterilizing chamber 111 is again surrounded by an annular distributing chamber 130 and there is also a connection 131 and 126.

I claim:

1. A method for sterilizing containers being fed to a filling and sealing machine for the containers, the filling and sealing machine having a sterile processing area, the method comprising the steps of:

providing a batch of the containers, each container in the batch having an open end oriented downwardly and each container being nested in at least one adjacent container, forming a stack, the containers being spaced by spacing structure between outer surfaces of one container and inner surfaces of a next container;

introducing the batch of the containers into a loading station attached to a sterilizing chamber, the sterilizing chamber having a sealable inlet and a sealable outlet including slidable doors, the outlet communicating directly with the filling and sealing machine when unsealed;

opening the inlet and transferring the batch of containers into the sterilizing chamber through the inlet while the outlet is kept sealed by transverse pressure on a door of the sealable outlet, the sterilizing chamber being isolated from the sterile processing area of the filling and sealing machine, the batch of containers remaining in the nested, downwardly-oriented attitude in the sterilizing chamber;

sealing the inlet by eccentric rollers which apply transverse pressure on a door of the sealable inlet and thereby isolating the sterilizing chamber;

sterilizing said batch of containers;

directly and sealably transferring the sterilized batch of containers into the filling and sealing machine by opening the outlet and transferring the batch of containers with the inlet kept closed and sealed by said transverse pressure on the door of the sealable inlet, the batch of containers being supported on a horizontal surface in the sterilization chamber, and the containers remaining in nested, downwardly-oriented attitude, whereby the containers, and the outlet through which the containers pass, remain sterile and the containers remain empty even though nested.

2. The method for sterilizing containers according to claim 1, wherein the containers are plastic cups, and further comprising the steps of separating individual cups from the batch, and inverting the individual cups, after sterilizing.

3. An apparatus for sterilizing containers prior to processing the containers in a filling and sealing machine, the apparatus comprising:

a stacking magazine for receiving a batch of said containers, the stacking magazine having a horizontal support for receiving a vertically-stacked batch of containers in a nested, downwardly-oriented attitude;

walls defining a sterilizing chamber having a tightly sealable inlet port and outlet port, the inlet port being disposed toward the stacking magazine and the outlet port being directly connected to an inlet of the filling and sealing machine, the walls holding the stack in vertical, downwardly-oriented position, the inlet port and the outlet port of the sterilizing chamber having slides movable to cover openings to the sterilizing chamber and having eccentric contact rollers mounted for urging the slides to seal the ports, the outlet port having a horizontal slide for supporting a vertically-stacked batch of the containers, the eccentric rollers being disposed along the slides and pressing the slides in a direction transverse to a direction of sliding;

means for controlling the inlet port and the outlet port in coordinated manner such that only one of the inlet port and the outlet port is openable at a given time;

an unstacking magazine for receiving the batch of containers from the sterilizing chamber, the unstacking magazine being disposed in the filling and sealing machine;

controllable connections for attaching the sterilizing chamber to sources of vacuum, sterilizing medium and sterile gas, and means for controlling said connections to sterilize contents of the chamber prior to opening of the outlet port.

4. An apparatus according to claim 3, further comprising means for connecting the sources of sterile gas and sterilizing agent to a distributing chamber surrounding a sterilizing area in the sterilizing chamber in an annular manner, the distributing chamber being connected to the sterilizing area by a plurality of openings adapted to pass the gas and sterilizing agent uniformly into the sterilizing chamber, the sterilizing area also having means for holding the batch in vertical downwardly-oriented attitude.

5. The apparatus according to claim 3, wherein the sterilizing chamber has a trough in a bottom thereof, and the vacuum sources connected to the sterilizing chamber at a lowest point of the trough.

6. The apparatus according to claim 3, wherein said containers are cups provided with stacking recesses and notches, the cups being held apart in the stack.

7. The method of claim 1, further comprising the step of evacuating the sterilizing chamber before said sterilizing step.

8. The method of claim 7, wherein said evacuating is accomplished using saturated steam.

9. The apparatus of claim 3, wherein the eccentric rollers are disposed along the slides and press the slides toward the sterilizing chamber of sliding.

10. The method of claim 7, wherein said evacuating step is accomplished before said sterilizing step.

11. The method of claim 7, further comprising a further evacuating step accomplished after said sterilizing step.

12. The method of claim 1, wherein the inlet and outlet are kept sealed by the eccentric rollers pressing the slides in a direction transverse to a direction of sliding.

13. The method of claim 12, wherein the eccentric rollers are operable to press the slides toward the sterilizing chamber.

14. An apparatus for sterilizing containers prior to processing the containers in a filling and sealing machine, the apparatus comprising:

a stacking magazine for receiving a batch of said containers, the stacking magazine having a horizontal support for receiving a vertically-stacked batch of containers in a nested, downwardly-oriented attitude;

walls defining a sterilizing chamber having a tightly sealable inlet port and outlet port, the inlet port being disposed toward the stacking magazine and the outlet port being directly connected to an inlet of the filling and sealing machine, the walls holding the stack in vertical, downwardly-oriented position, and the inlet port and outlet port having more to close said parts and eccentric contact rollers arranged on each end of the sterilizing chamber adjacent said closing means, means for turning said eccentric rollers to apply pressure toward said chamber to seal said chamber, an eccentric roller for the inlet port being disposed at a lower end of the stacking magazine;

means for controlling the inlet port and the outlet port in coordinated manner such that only one of the inlet port and the outlet port is openable at a given time;

an unstacking magazine adjacent said outlet port and said eccentric roller, for receiving the batch of containers from the sterilizing chamber, the unstacking magazine being disposed in the filling and sealing machine;

controllable connections for attaching the sterilizing chamber to sources of vacuum, sterilizing medium and sterile gas, and means for controlling said connections to sterilize contents of the chamber prior to opening of the outlet port.

* * * * *